United States Patent
Ito

(10) Patent No.: US 8,303,492 B2
(45) Date of Patent: Nov. 6, 2012

(54) ENDOSCOPE APPARATUS

(75) Inventor: Hiroshi Ito, Hachioji (JP)

(73) Assignee: Olympus Corporation, Tokyo (JP)

( * ) Notice: Subject to any disclaimer, the term of this patent is extended or adjusted under 35 U.S.C. 154(b) by 855 days.

(21) Appl. No.: 12/424,205

(22) Filed: Apr. 15, 2009

(65) Prior Publication Data

US 2009/0264701 A1  Oct. 22, 2009

(30) Foreign Application Priority Data

Apr. 16, 2008  (JP) ................................. 2008-107037

(51) Int. Cl.
*A61B 1/00* (2006.01)
*G02B 23/24* (2006.01)
*G02B 23/26* (2006.01)

(52) U.S. Cl. ....................................... 600/176; 600/129

(58) Field of Classification Search ...... 128/6; 600/129, 600/176; 264/1.21; 385/117; 367/155
See application file for complete search history.

(56) References Cited

U.S. PATENT DOCUMENTS

| | | | | |
|---|---|---|---|---|
| 4,385,255 A * | 5/1983 | Yamaguchi et al. | ........... | 310/335 |
| 4,870,950 A * | 10/1989 | Kanbara et al. | ............... | 600/109 |
| 4,992,692 A * | 2/1991 | Dias | ............................. | 310/335 |
| 5,425,123 A * | 6/1995 | Hicks | ............................. | 385/117 |
| 5,685,311 A * | 11/1997 | Hara | ............................. | 600/459 |
| 5,884,627 A * | 3/1999 | Wakabayashi et al. | ........ | 600/447 |
| 5,980,454 A * | 11/1999 | Broome | ......................... | 600/176 |
| 5,995,453 A * | 11/1999 | Hirata | ........................... | 367/155 |
| 7,245,193 B2 * | 7/2007 | Funasaka | ....................... | 333/193 |
| 7,696,671 B2 * | 4/2010 | Sawada et al. | ................ | 310/334 |
| 8,016,753 B2 * | 9/2011 | Sugita | ............................ | 600/156 |
| 8,025,818 B2 * | 9/2011 | Alkemper et al. | ............ | 264/1.21 |
| 8,066,643 B2 * | 11/2011 | Imahashi et al. | .............. | 600/459 |
| 2008/0200814 A1 * | 8/2008 | Imahashi et al. | .............. | 600/463 |

FOREIGN PATENT DOCUMENTS

| | | | |
|---|---|---|---|
| JP | 05-207962 | | 8/1993 |
| JP | 2006-055275 | * | 3/2006 |
| JP | 2006-55275 | | 3/2006 |

* cited by examiner

*Primary Examiner* — Clayton E LaBalle
*Assistant Examiner* — Kevin Butler
(74) *Attorney, Agent, or Firm* — Scully, Scott, Murphy & Presser, PC

(57) ABSTRACT

An endoscope apparatus includes a transparent member provided at a distal end of an insertion portion of an endoscope to face an image pickup optical system, an ultrasonic transducer attached to an inner surface of the transparent member, and a deflection portion provided at an outer surface of the transparent member which changes a direction of propagation of an ultrasonic wave from the ultrasonic transducer. With the configuration, an ultrasonic wave for stain removal is efficiently propagated from the ultrasonic transducer into a region of an observation field of view in an observation window.

13 Claims, 14 Drawing Sheets

ENDOSCOPE APPARATUS

This application claims benefit of Japanese application No. 2008-107037 filed in Japan on Apr. 16, 2008, the contents of which are incorporated by this reference.

BACKGROUND OF THE INVENTION

1. Field of the Invention

The present invention relates to an endoscope apparatus which achieves an improvement in observability by easily removing a stain deposited on a surface of an observation window and, more specifically, to a surgical endoscope apparatus.

2. Description of the Related Art

In recent years, surgery using an endoscope has come into widespread use for purposes of minimally invasive medicine. Prevention of deterioration in observation environment caused by deposition of a stain on or generation of a fog on an observation window disposed at a distal end portion of an endoscope presents a challenge to such endoscopic surgery.

In some endoscopes for digestive organs, a fog or a stain is removed by supplying water to a lens at an endoscope distal end portion. A stain deposited on a surgical endoscope may be blood, fat, or the like scattered during surgery, and the stain may not be removed by simply supplying water.

For example, a technique disclosed in Japanese Patent Application Laid-Open Publication No. 2006-55275 has been known as a measure to be taken against the above-described problem.

In the conventional endoscope apparatus, a cover glass serving as an image capture window is attached to a distal end of an inner tube of an insertion portion to face an objective optical system. A coating layer which is a hydrophilically treated layer made of a photocatalyst (e.g., titanium oxide) and having an affinity for water is formed on an outer surface of the cover glass.

When dew condensation occurs on the cover glass due to a difference in temperature from a surrounding environment, the affinity for water of the coating layer diffuses water particles and forms a thin water film, which prevents a fog on the surface. That is, the formation of the water film prevents a fog on the outer surface of the cover glass and returns the cover glass to an initial state, a state in which a clear field of view is ensured. When a stain such as bodily fluids or a splash from a radio knife (not shown) comes into contact with the water film formed on the coating layer of the cover glass, the stain is deposited on the water film.

At the inner tube of the insertion portion, an ultrasonic transducer is provided to be capable of transmitting vibration to the cover glass. When the ultrasonic transducer is driven and controlled, the ultrasonic transducer generates an ultrasonic wave, and the ultrasonic wave is propagated to the cover glass. In the conventional endoscope apparatus, the ultrasonic wave propagated to the cover glass and action of gravity cause the water film formed on the coating layer on the outer surface of the cover glass to drop and be removed. At the time, a stain deposited on the water film drops together with the water film, and the outer surface of the cover glass is cleaned. Note that a water film can also be formed by supplying water onto the coating layer by a water supply nozzle or the like.

However, in the conventional endoscope apparatus, the ultrasonic transducer at the inner tube is attached to a peripheral part, i.e., an inner surface of the inner tube except for a part facing the objective optical system such that the ultrasonic transducer does not interfere with an observation field of view. That is, a region of the observation field of view of an observation window (the cover glass) is separate from the part where the ultrasonic transducer is attached. Depending on the part where the ultrasonic transducer is attached, an ultrasonic wave from the ultrasonic transducer may not be easily transmitted to the region of the observation field of view (an ultrasonic wave propagates with high intensity in a direction perpendicular to the surface where the ultrasonic transducer is attached, and the tendency is especially noticeable in the case of a high-frequency ultrasonic wave), and a stain deposited on the observation window may not be sufficiently removed.

SUMMARY OF THE INVENTION

An endoscope apparatus according to the present invention includes a transparent member provided at a distal end of an insertion portion of an endoscope to face an image pickup optical system, an ultrasonic transducer attached to an inner surface of the transparent member, and a deflection portion provided at an outer surface of the transparent member which changes a direction of propagation of an ultrasonic wave from the ultrasonic transducer. This makes it possible to efficiently propagate an ultrasonic wave for stain removal from an ultrasonic transducer into a region of an observation field of view in an observation window and allows positive removal of a stain deposited on the observation window.

The above and other objects, features and advantages of the invention will become more clearly understood from the following description referring to the accompanying drawings.

DETAILED DESCRIPTION OF THE PREFERRED EMBODIMENTS

First Embodiment

A first embodiment of the present invention will be described below with reference to the drawings. Note that a rigid endoscope for laparoscopic surgery will be illustrated by way of example in a following description.

Figure 1:
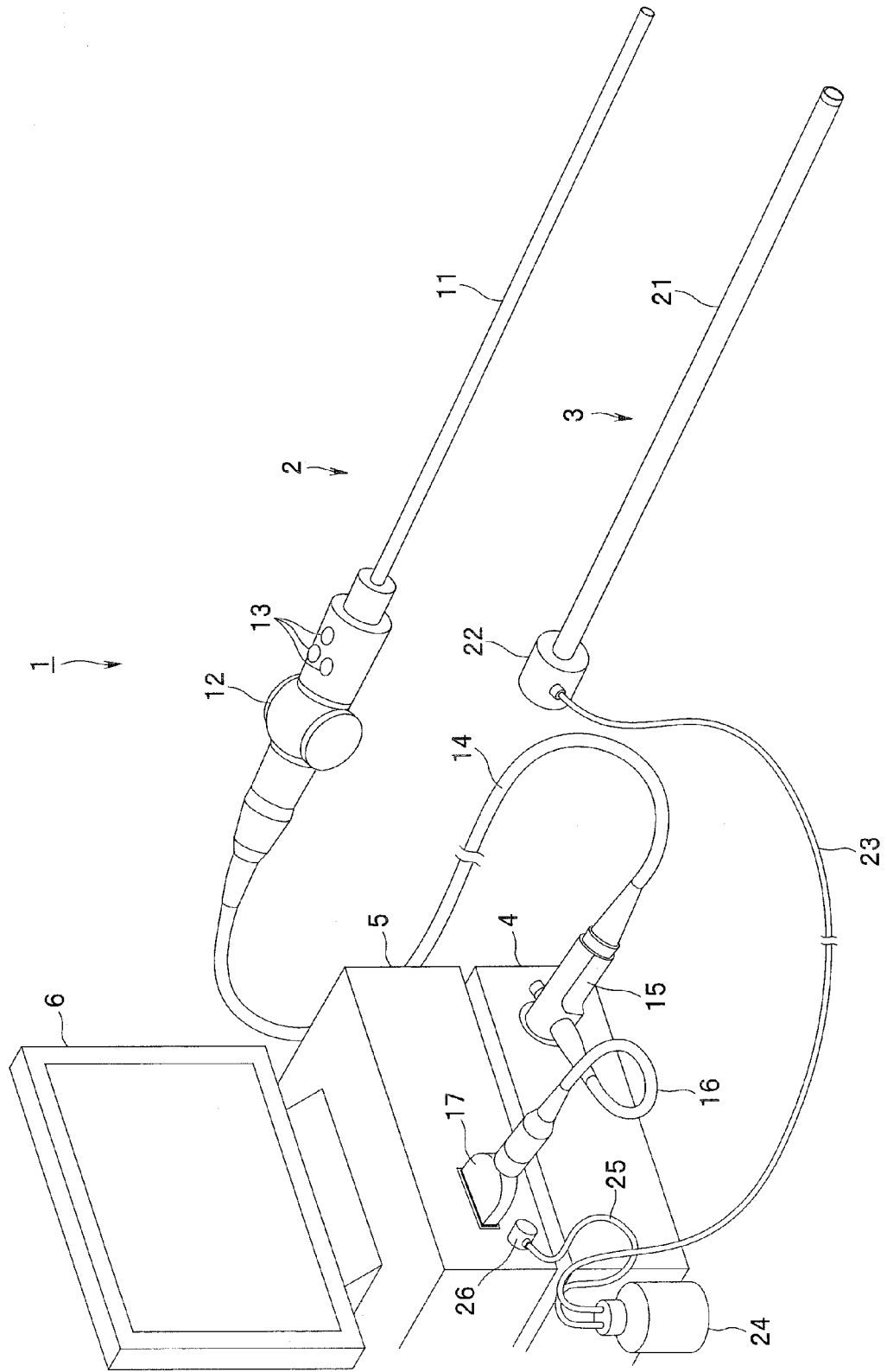
FIG. 1 is a view of an overall configuration of an endoscope system according to a first embodiment of the present invention.
Figure 2:
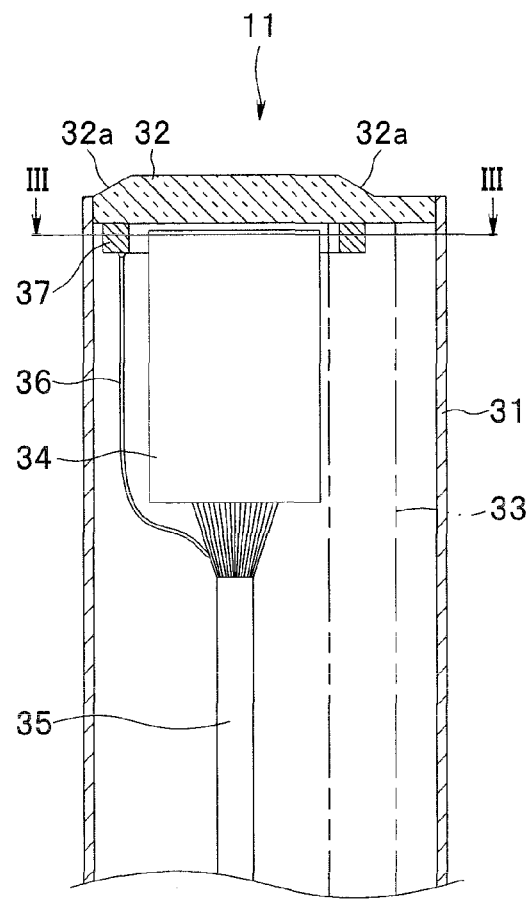
FIG. 2 is a cross-sectional view showing a configuration of a distal end portion of a rigid endoscope, according to the first embodiment.
Figure 3:
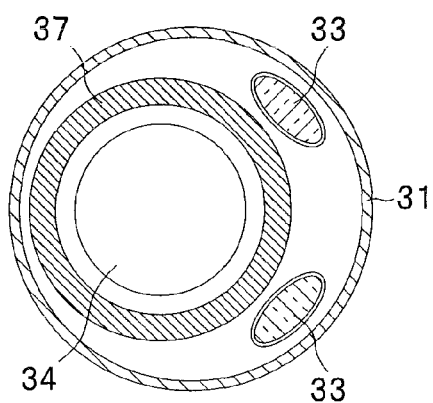
FIG. 3 is a cross-sectional view of the distal end portion taken along line III-III in FIG. 2, according to the first embodiment.
Figure 4:
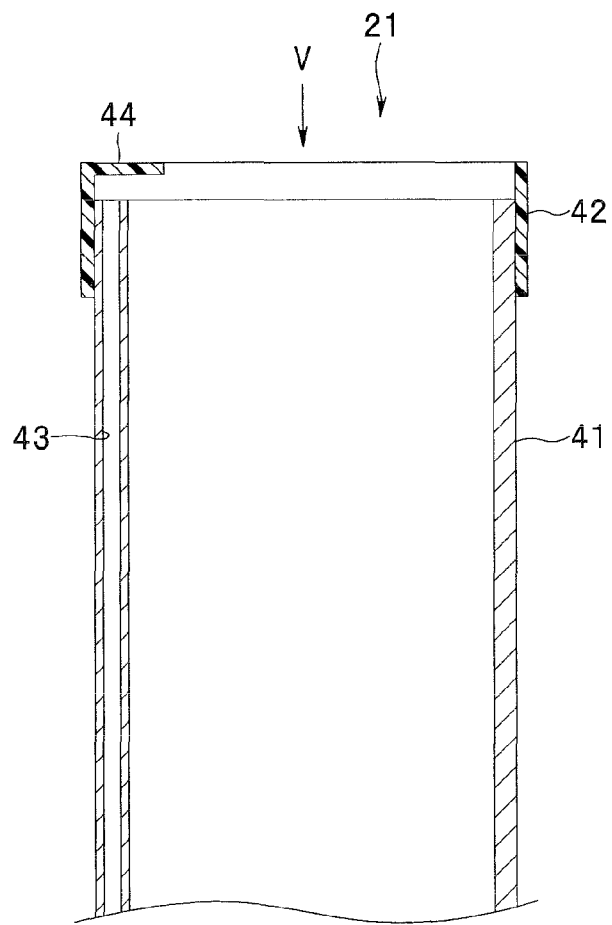
FIG. 4 is a cross-sectional view showing a configuration of a distal end portion of a water supply sheath, according to the first embodiment.
Figure 5:
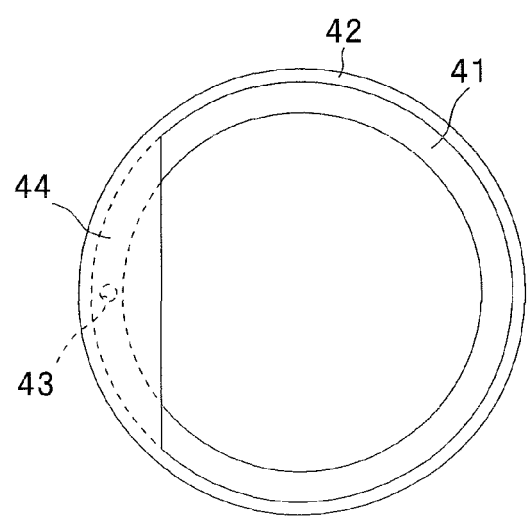
FIG. 5 is a view showing a configuration of the water supply sheath as seen in a direction indicated by an arrow V in FIG. 4, according to the first embodiment.
Figure 6:
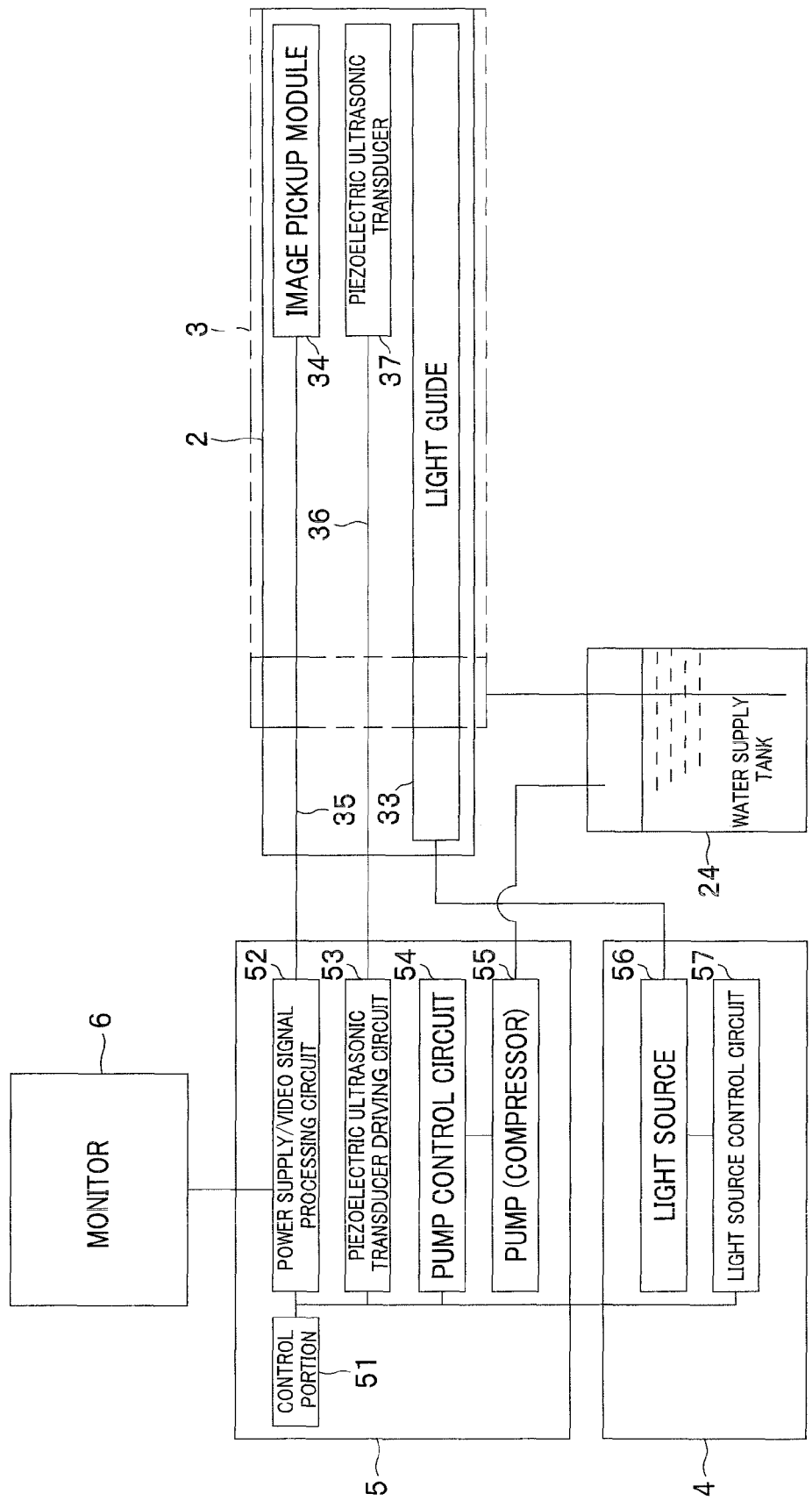
FIG. 6 is a block diagram mainly showing an electrical configuration of the endoscope system, according to the first embodiment.
Figure 7:
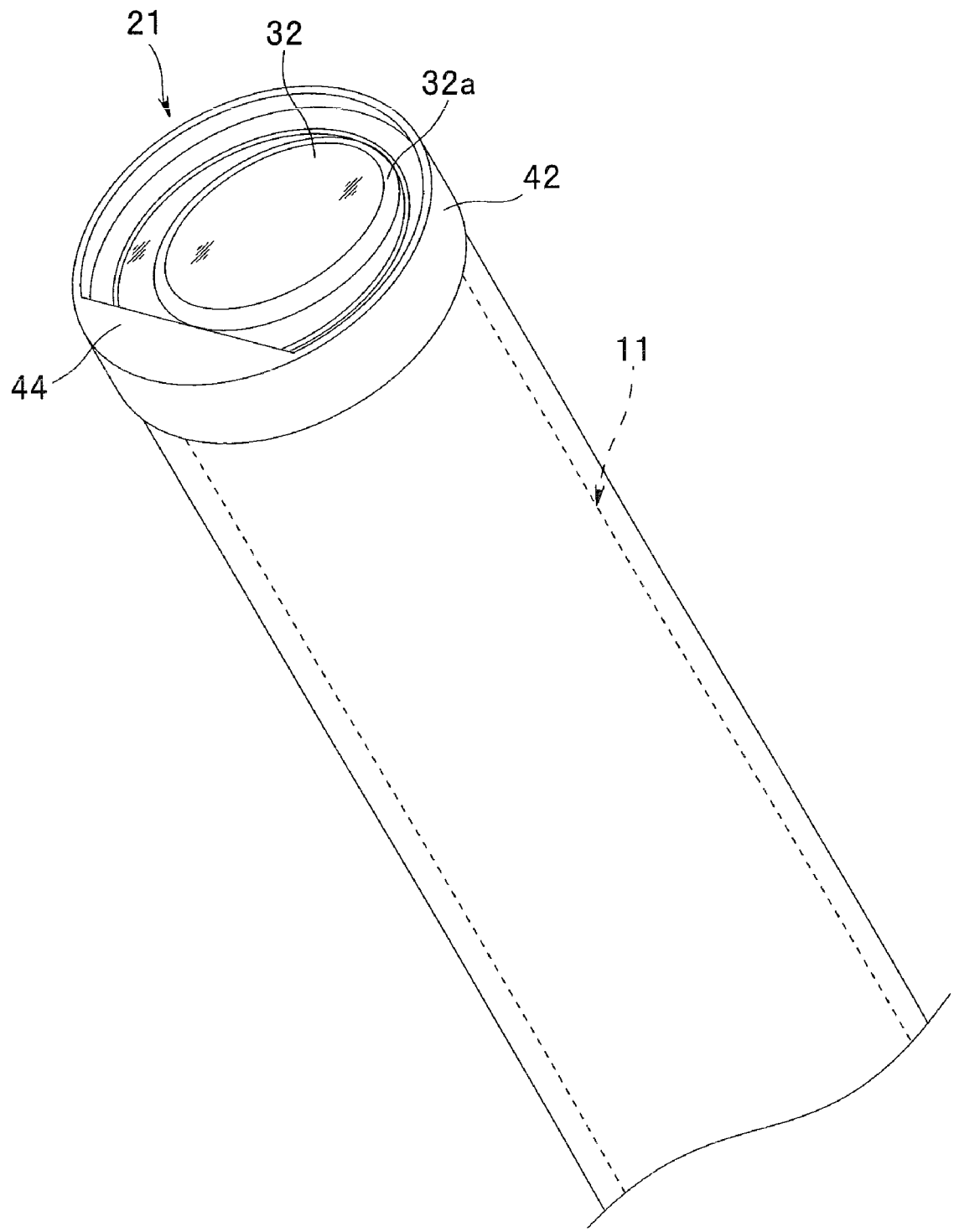
FIG. 7 is a perspective view of a distal end portion showing a state in which an insertion portion of the rigid endoscope is inserted through the water supply sheath, according to the first embodiment.
Figure 8:
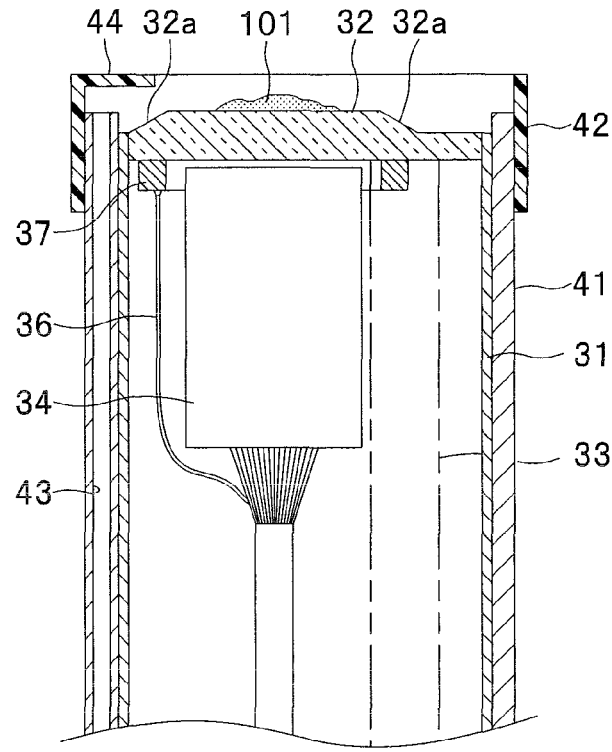
FIG. 8 is a cross-sectional view of the distal end portion showing a state in which the insertion portion of the rigid endoscope is inserted through the water supply sheath and is a view showing a state in which a deposit is on an observation window, according to the first embodiment.
Figure 9:
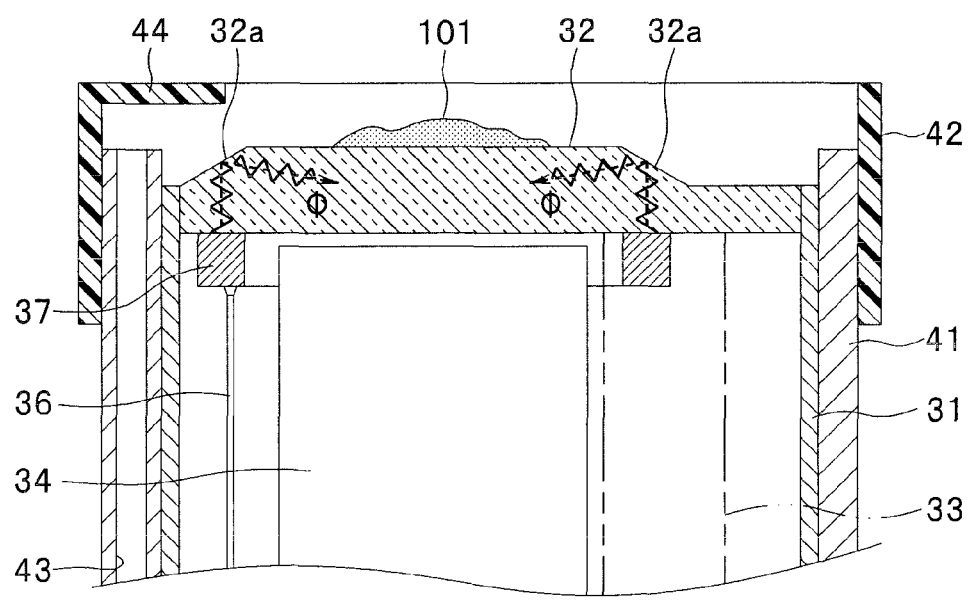
FIG. 9 is a cross-sectional view showing a state in which a wave from a piezoelectric ultrasonic transducer is deflected by a deflection portion formed at an outer surface of the observation window and propagates through the observation window, according to the first embodiment.
Figure 10:
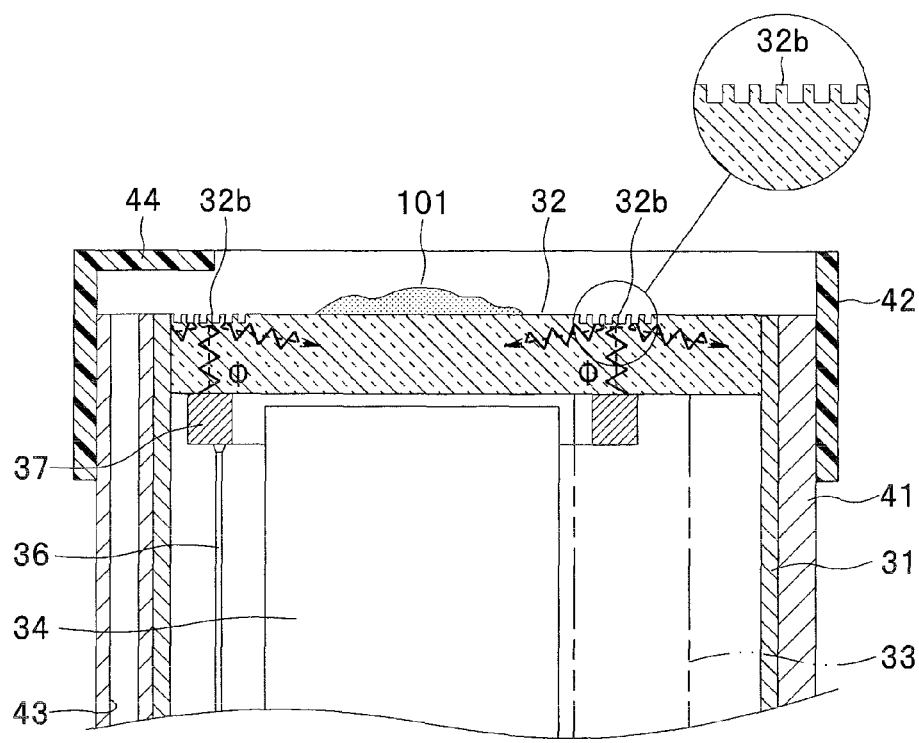
FIG. 10 shows a first modification of the first embodiment and is a cross-sectional view showing a state in which a rectangular grating-like deflection portion is formed at the outer surface of the observation window, and a wave from the piezoelectric ultrasonic transducer propagates to the observation window.
Figure 11:
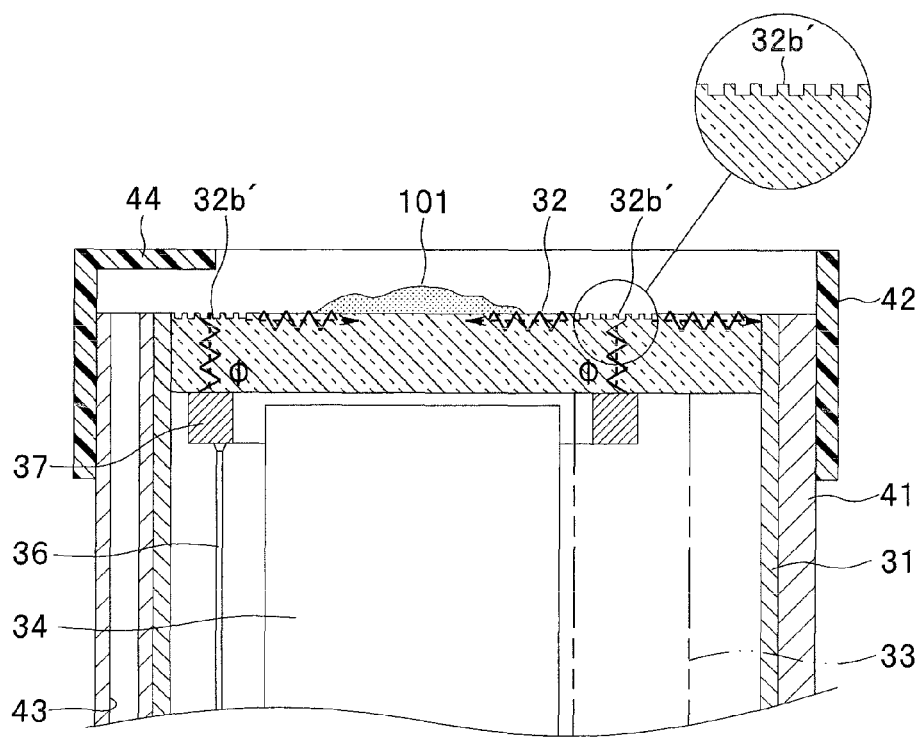
FIG. 11 shows a second modification of the first embodiment and is a cross-sectional view showing a state in which a wave from the piezoelectric ultrasonic transducer which has been converted into a surface acoustic wave by a rectangular grating-like deflection portion with a specific period propagates at the outer surface of the observation window.
Figure 12:
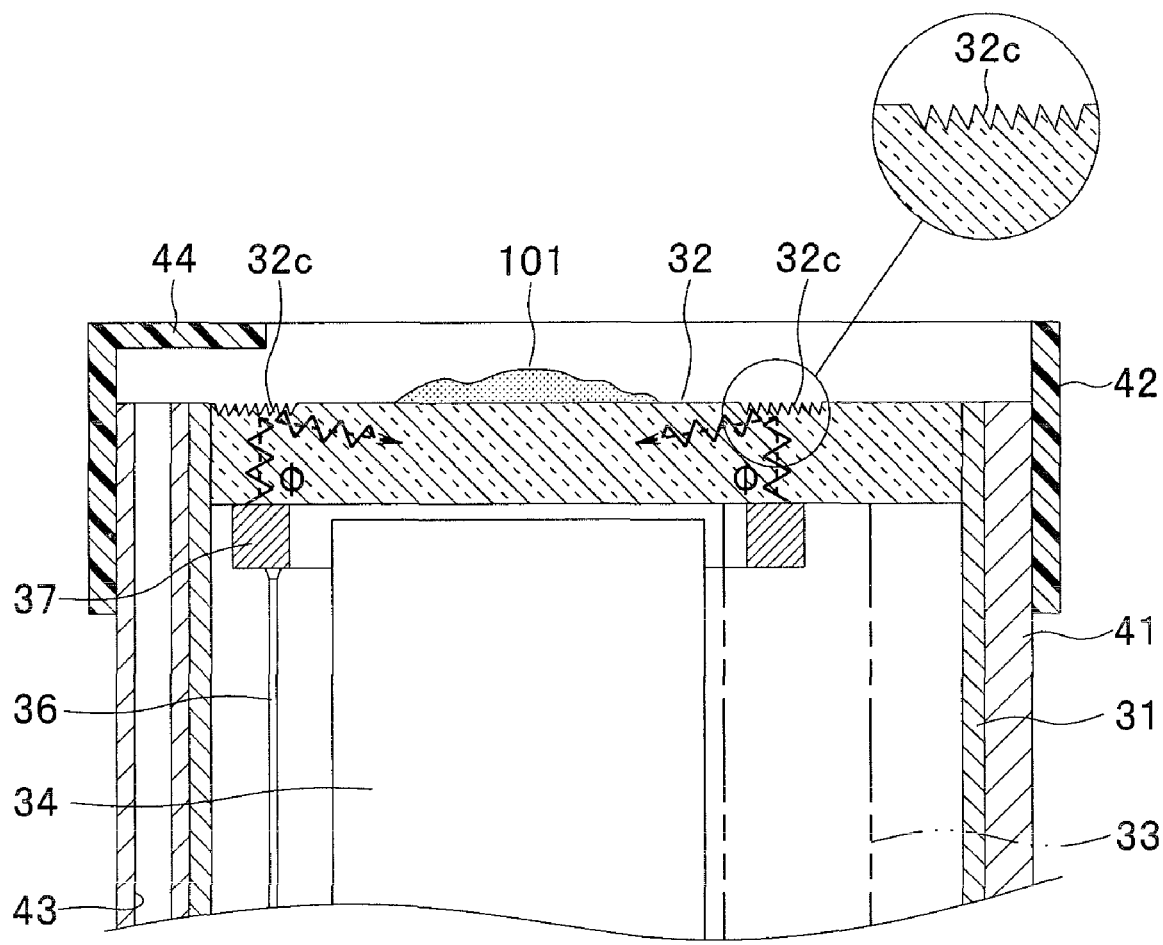
FIG. 12 shows a third modification of the first embodiment and is a cross-sectional view showing a state in which a blazed grating-like deflection portion is formed at the outer surface of the observation window, and a wave from the piezoelectric ultrasonic transducer propagates through the observation window.

FIGS. 1 to 12 relate to the first embodiment of the present invention. FIG. 1 is a view of an overall configuration of an endoscope system. FIG. 2 is a cross-sectional view showing a configuration of a distal end portion of a rigid endoscope. FIG. 3 is a cross-sectional view of the distal end portion taken along line III-III in FIG. 2. FIG. 4 is a cross-sectional view showing a configuration of a distal end portion of a water supply sheath. FIG. 5 is a view showing a configuration of the water supply sheath as seen in a direction indicated by an arrow V in FIG. 4. FIG. 6 is a block diagram mainly showing an electrical configuration of the endoscope system. FIG. 7 is a perspective view of a distal end portion showing a state in which an insertion portion of the rigid endoscope is inserted through the water supply sheath. FIG. 8 is a cross-sectional view of the distal end portion showing a state in which the insertion portion of the rigid endoscope is inserted through the water supply sheath and is a view showing a state in which a deposit is on an observation window. FIG. 9 is a cross-sectional view showing a state in which a wave from a piezoelectric ultrasonic transducer is deflected by a deflection portion formed at an outer surface of the observation window and propagates to a region of an observation field of view in the observation window. FIG. 10 shows a first modification and is a cross-sectional view showing a state in which a wave from the piezoelectric ultrasonic transducer is changed in a direction of propagation by a rectangular grating-like deflection portion provided at the outer surface of the observation window and propagates to the region of the observation field of view in the observation window. FIG. 11 shows a second modification and is a cross-sectional view showing a state in which a wave from the piezoelectric ultrasonic transducer is converted into a surface acoustic wave which propagates at the outer surface of the observation window by a grating-like deflection portion with a specific period (to be described later) provided at the outer surface of the observation window and propagates to the region of the observation field of view in the observation window. FIG. 12 shows a third modification and is a cross-sectional view showing a state in which a wave from the piezoelectric ultrasonic transducer is changed in a direction of propagation by a blazed grating-like deflection portion provided at the outer surface of the observation window and propagates to the region of the observation field of view in the observation window.

As shown in FIG. 1, an endoscope system 1 which is an endoscope apparatus according to the present embodiment is mainly composed of a rigid endoscope (hereinafter simply referred to as an endoscope) 2, a water supply sheath 3 constituting cleaning solution supply means through which an insertion portion 11 of the endoscope 2 is inserted, a video processor 5, a light source device 4, and a monitor 6.

The endoscope 2 is configured to have the rigid insertion portion 11, an operation portion 12 connected in series with the insertion portion 11, switches and other components 13 provided at the operation portion 12, a universal cable 14 extending from the operation portion 12, a light source connector 15 disposed at an extension end of the universal cable 14, a composite cable 16 extending from a side portion of the light source connector 15, and an electric cable 17 disposed at an extension end of the composite cable 16.

Note that the light source connector 15 is detachably connected to the light source device 4. Also note that the electric cable 17 is detachably connected to the video processor 5.

The water supply sheath 3 is configured to have a cover tube 21 including a distal end member (to be described later), a connection portion 22 connected in series with the cover tube 21, and a water supply tube 23 extending from a side portion of the connection portion 22. Note that an extension end of the water supply tube 23 is connected to a water supply tank 24. The other end of an air supply tube 25 whose one end is connected to an air supply connector 26 of the video processor 5 is connected to the water supply tank 24.

The video processor 5 is electrically connected to the light source device 4 and monitor 6. The video processor 5 converts image data picked up by the endoscope 2 into a video signal and causes the monitor 6 to display the video signal. The video processor 5 constitutes a control device serving as control means for, upon receipt of an operation signal inputted with the switches and other components 13 disposed at the operation portion 12 of the endoscope 2, controlling the light source device 4 or feeding air to the water supply tank 24 and controlling feeding of cleaning water such as normal saline in the water supply tank 24 to the water supply sheath 3, in accordance with the signal.

A configuration of a distal end portion of the insertion portion 11 of the endoscope 2 will be described below with reference to FIGS. 2 and 3.

In the insertion portion 11 of the endoscope 2, a glass plate 32 of a transparent member serving as an observation window is coupled to a distal end of a tubular member 31 made of a metal, as shown in FIGS. 2 and 3. An image pickup module 34 and two illuminating light guides 33 are arranged inside the tubular member 31. Although not shown in detail, an imaging optical system, a solid-state image pickup device, and a driver chip for the solid-state image pickup device are incorporated in the image pickup module 34 constituting an image pickup optical system, and communication cables 35 are led out toward a base.

A ring-like piezoelectric ultrasonic transducer 37 is attached to a back surface of the glass plate 32 to surround a part facing a distal end portion of the image pickup module 34. The piezoelectric ultrasonic transducer 37 may have a perfectly annular shape or have a partially cut annular shape which surrounds an outer peripheral portion spaced apart from an observation region by a predetermined distance in the glass plate 32. Fixation of the piezoelectric ultrasonic transducer 37 to the glass plate 32 is not limited to fixation with adhesive agent and may be fixation with solder or the like.

The piezoelectric ultrasonic transducer 37 is driven at a resonant frequency or around the resonant frequency and generates an ultrasonic wave inside the glass plate 32. In the glass plate 32, an inclined surface 32a is provided at a position of an outer surface facing the piezoelectric ultrasonic transducer 37 attached to an inner surface (the back surface). An electric cable 36 for supplying a voltage for producing vibration is led out from the piezoelectric ultrasonic transducer 37 toward the base of the endoscope 2.

The inclined surface 32a constitutes a deflection portion which deflects an ultrasonic wave from the piezoelectric ultrasonic transducer 37 toward a center of the glass plate 32 and is a ring-like tapered surface which slopes down from the center of the glass plate 32 toward an outer edge. An angle of the taper is set in consideration of a thickness of the glass plate 32 and a shape and an area of a region serving as the deflection portion such that an ultrasonic wave efficiently reaches a region of an observation field of view. Note that the center of the glass plate 32 here refers to a center of a part facing the image pickup system of the image pickup module 34 of the glass plate 32 which is a position at which an optical axis of the image pickup optical system passes through the glass plate 32.

The thickness of the glass plate 32 is larger inside the inclined surface 32a than outside the inclined surface 32a.

As for a position of the inclined surface 32a relative to the piezoelectric ultrasonic transducer 37, at least a part of a surface of the piezoelectric ultrasonic transducer 37 needs to be within a projection region of the inclined surface 32a when the inclined surface 32a is projected from the surface (outer surface) where the inclined surface 32a is formed onto the surface (inner surface) of the glass plate 32 where the piezoelectric ultrasonic transducer 37 is attached, in view of efficiently causing an ultrasonic wave from the piezoelectric ultrasonic transducer 37 to propagate into the glass plate 32.

Preferably, the piezoelectric ultrasonic transducer 37 is entirely within the projection region.

Note that the light guides 33, communication cables 35, and electric cable 36 are provided to pass through the operation portion 12 shown in FIG. 1 and extend through the universal cable 14. Also note that the light guides 33 terminate at the light source connector 15, and the communication cables 35 and electric cable 36 are connected to the electric cable 17 via the composite cable 16.

The components of the endoscope 2 are sealed with the tubular member 31 and the glass plate 32 coupled to the tubular member 31, and the endoscope 2 is structured to be resistant to autoclave sterilization.

Although the part facing the image pickup optical system of the image pickup module 34 of the glass plate 32 is planar in the present embodiment, a part of the facing part may be convex or concave and constitute a part of the image pickup optical system.

The water supply sheath 3 will be described below with reference to FIGS. 4 and 5.

The cover tube 21 of the water supply sheath 3 is configured to have a tube main body 41 and an almost cylindrical distal end member 42 fit in a distal end of the tube main body 41. One water supply line 43 for water supply is formed in a part of a thick part of the tube main body 41. The water supply line 43 is disposed to reach the connection portion 22 shown in FIG. 1 and communicates with the water supply tube 23 via the connection portion 22.

The distal end member 42 has a hooded portion 44 which is a plate at a position facing the water supply line 43 of the tube main body 41 along an end face of an opening.

The endoscope system 1 will be described below with a main focus on an electrical configuration with respect to FIG. 6.

As shown in FIG. 6, the video processor 5 is configured to have a control portion 51 serving as a CPU, a power supply/video signal processing circuit 52, a piezoelectric ultrasonic transducer driving circuit 53, a pump control circuit 54, and a pump 55 serving as a compressor.

The control portion 51 is electrically connected to the power supply/video signal processing circuit 52, piezoelectric ultrasonic transducer driving circuit 53, and pump control circuit 54 and controls the circuits. The power supply/video signal processing circuit 52 is also electrically connected to the monitor 6 and outputs an endoscope image signal to the monitor 6.

The piezoelectric ultrasonic transducer driving circuit 53 has a function of vibrating the piezoelectric ultrasonic transducer 37 of the endoscope 2 and variably controls vibration intensity of the piezoelectric ultrasonic transducer 37 according to the amount of electric power to be outputted under control of the control portion 51.

The pump control circuit 54 is electrically connected to the pump 55 and outputs an electric signal for driving and controlling the pump 55 under control of the control portion 51.

The light source device 4 is configured to have a light source 56 such as a halogen lamp and a light source control circuit 57 which drives the light source 56. The light source control circuit 57 is electrically connected to the control portion 51 of the video processor 5 and is controlled by the control portion 51.

Only the distal end portion of the endoscope 2 is shown in FIGS. 2 and 3. However, in the endoscope 2, the light guides 33 are connected to the light source 56 of the light source device 4 including the light source control circuit 57, the communication cables 35 led out from the image pickup module 34 are connected to the power supply/video signal processing circuit 52 of the video processor 5, and the electric cable 36 led out from the piezoelectric ultrasonic transducer 37 is connected to the piezoelectric ultrasonic transducer driving circuit 53 constituting driving means (vibration means) of the video processor 5, via the universal cable 14 connected to the operation portion 12 and the composite cable 16.

In the water supply sheath 3, the water supply line 43 is connected to the water supply tank 24, and cleaning water in the water supply tank 24, i.e., normal saline or the like is fed to the distal end portion of the endoscope through the water supply line 43 by the pump 55 controlled by the pump control circuit 54.

In the endoscope system 1 according to the present embodiment with the above-described configuration, the insertion portion 11 of the endoscope 2 is inserted through the cover tube 21 of the water supply sheath 3, as shown in FIG. 7. The endoscope system 1 is used for, e.g., laparoscopic surgery.

If a stain 101 such as blood or fat is deposited on the outer surface of the glass plate 32 in the endoscope system 1 during surgery, as shown in FIG. 8, an operator who is a doctor operates a remote switch in the switches and other components 13 provided at the operation portion 12 of the endoscope 2. In response to a control signal generated by the switch operation, an excitation signal is supplied from the piezoelectric ultrasonic transducer driving circuit 53 of the video processor 5 to the piezoelectric ultrasonic transducer 37, and an ultrasonic wave is generated in the glass plate 32.

Prior to the generation of the ultrasonic wave, cleaning water is supplied from the water supply sheath 3 to the outer surface of the glass plate 32 by the operation of the switches and other components 13. That is, air is supplied from the pump 55 serving as the compressor into the water supply tank 24, and the cleaning water in the water supply tank 24 is supplied to the water supply sheath 3. The cleaning water is ejected from the distal end of the tube main body 41 via the water supply line 43 formed in the tube main body 41 of the water supply sheath 3, strikes the hooded portion 44, and flows out along an almost whole of the outer surface of the glass plate 32.

As shown in FIG. 9, an ultrasonic wave $\phi$ generated at an ultrasonic wave emitting surface serving as a vibrating surface, i.e., the inner surface (back surface) of the glass plate 32 where the piezoelectric ultrasonic transducer 37 is attached propagates in an almost vertical direction inside the glass plate 32, is deflected in an oblique direction by the inclined surface 32a, and propagates in a lateral direction toward the center of the glass plate 32 (the center of the part facing the image pickup system of the image pickup module 34 of the glass plate 32). Note that deflecting the ultrasonic wave $\phi$ by the inclined surface 32a and causing the ultrasonic wave $\phi$ to propagate in the lateral direction is effective regardless of a frequency of the ultrasonic wave and is particularly effective when the frequency is high.

In other words, at a high frequency, directivity of the ultrasonic wave $\phi$ is high, most of vibration energy travels straight in a direction perpendicular to the planar surface of the piezoelectric ultrasonic transducer 37 (the surface at which a wave is emitted from the piezoelectric ultrasonic transducer 37 and at which the piezoelectric ultrasonic transducer 37 is attached to the inner surface of the glass plate 32). Accordingly, if the inclined surface 32a serving as the deflection portion is not provided in the glass plate 32, since the directivity of the ultrasonic wave $\phi$ is high, the ultrasonic wave $\phi$ is repeatedly reflected between the planar surface of the piezoelectric ultrasonic transducer 37 and a part of the outer surface of the glass plate 32 facing the planar surface of the piezoelectric ultrasonic transducer 37. The ultrasonic wave $\phi$ is transmitted well to the facing part while the wave is not transmitted well to a part other than the facing part, i.e., a region of the glass plate 32 separate from the piezoelectric ultrasonic transducer 37.

In contrast, if the inclined surface 32a serving as the deflection portion is provided at the glass plate 32, like the present embodiment, the ultrasonic wave $\phi$ travelling straight from the piezoelectric ultrasonic transducer 37 is deflected toward a center of an observation region of the image pickup module 34 in the glass plate 32 by the inclined surface 32a provided at the outer surface of the glass plate 32. That is, of the generated ultrasonic waves $\phi$, at least some that have come incident on the inclined surface 32a are deflected toward a photographing optical axis. The inclined surface 32a allows efficient propagation of even a high-frequency ultrasonic wave with high directivity toward the center of the glass plate 32. The stain 101 deposited on the outer surface is mixed with cleaning water, a part of the stain 101 mixed with the cleaning water is atomized, and another part is washed away. This makes it possible to efficiently and positively remove the stain 101 across an almost whole surface of the observation region in the glass plate 32.

As has been described above, in the endoscope system 1 according to the present embodiment, it is possible to efficiently remove the stain 101 on the outer surface of the glass plate 32 facing the image pickup module 34 of the endoscope 2, especially in the region of the observation field of view by deflecting the ultrasonic wave $\phi$ from the piezoelectric ultrasonic transducer 37 by the inclined surface 32a serving as the deflection portion provided at the glass plate 32 and efficiently propagating the ultrasonic wave $\phi$ toward the center of the glass plate 32, i.e., a center of a part facing the region of the observation field of view of the image pickup module 34.

Note that a deflection portion composed of grooves whose cross-sectional shapes are rectangular or blazed (i.e., a rectangular grating or a blazed grating) may be formed at the outer surface of the glass plate 32 instead of the inclined surface 32a, as shown in FIG. 10 (a first modification), FIG. 11 (a second modification), and FIG. 12 (a third modification) as modifications.

More specifically, as shown in FIG. 10, grating-like grooves 32b whose cross-sectional shapes are rectangular are formed as the deflection portion at the outer surface of the glass plate 32 of the endoscope 2. At least a part of the surface of the piezoelectric ultrasonic transducer 37 is located within a projection region of the grooves 32b when the grooves 32b are projected from the surface (outer surface) where the grating-like grooves 32b are formed onto the surface (inner surface) of the glass plate 32 where the piezoelectric ultrasonic transducer 37 is attached. In the glass plate 32, the ultrasonic waves $\phi$ generated by the piezoelectric ultrasonic transducer 37 are diffracted (deflected) by the grating-like grooves 32b, and at least some of the ultrasonic waves $\phi$ propagate efficiently toward the above-described center of the glass plate 32, i.e., the center of the part facing the region of the observation field of view of the image pickup module 34.

With the configuration, it is possible to remove the stain 101 across a whole of the outer surface facing the region of the observation field of view of the image pickup module 34 of the glass plate 32, like the case where the inclined surface 32a is provided as the deflection portion. Note that, in the case of the grating-like grooves 32b whose cross-sectional shapes are rectangular, a diffraction (deflection) direction of the ultrasonic wave $\phi$ and vibration intensity at the time of diffraction can be changed by appropriately setting a grating spacing and a depth. That is, with the above-described setting, it is possible to propagate a diffracted wave of a specific order of diffracted waves generated by the grating-like grooves 32b toward the above-described center of the glass plate 32 with appropriate intensity in a desired direction.

Especially if the grating spacing (grating period) is set to about a value obtained by dividing velocity of a surface acoustic wave which propagates at the surface of the glass plate 32 by a frequency of the ultrasonic wave ϕ incident on the grating, the ultrasonic wave ϕ incident on grating-like grooves 32b' can be mode-converted into a surface acoustic wave which propagates at the outer surface of the glass plate 32, as shown in FIG. 11. Since the surface acoustic wave propagates with vibration concentrated on the surface of the glass plate 32, it is possible to efficiently transmit vibration to the stain 101 deposited on the outer surface of the glass plate 32 and remove the stain 101.

Alternatively, blazed grating-like grooves 32c may be formed as the deflection portion at the outer surface of the glass plate 32 of the endoscope 2, as shown in FIG. 12. The grooves 32c are located such that at least a part of the surface of the piezoelectric ultrasonic transducer 37 is located within a projection region of the grooves 32c when the grooves 32c are projected from the surface (outer surface) where the grooves 32c are formed onto the surface (inner surface) of the glass plate 32 where the piezoelectric ultrasonic transducer 37 is attached.

The ultrasonic waves ϕ from the piezoelectric ultrasonic transducer 37 propagating through the glass plate 32 are diffracted (deflected) by the blazed grating-like grooves 32c, thereby allowing efficient propagation of almost all of the ultrasonic waves ϕ toward the above-described center of the glass plate 32, i.e., the center of the part facing the observation field of view of the image pickup module 34.

This makes it possible to remove the stain 101 across a whole of the outer surface facing the observation field of view of the image pickup module 34 in the glass plate 32, like the above-described configuration. Note that the blazed grating-like grooves 32c can concentrate only ones of the specific order of diffracted waves, as compared to the rectangular grating-like grooves 32b in FIG. 10. Accordingly, the ultrasonic wave ϕ incident on the grooves 32c can be more efficiently propagated toward the above-described center of the glass plate 32 separate from the piezoelectric ultrasonic transducer 37.

Second Embodiment

Figure 13:
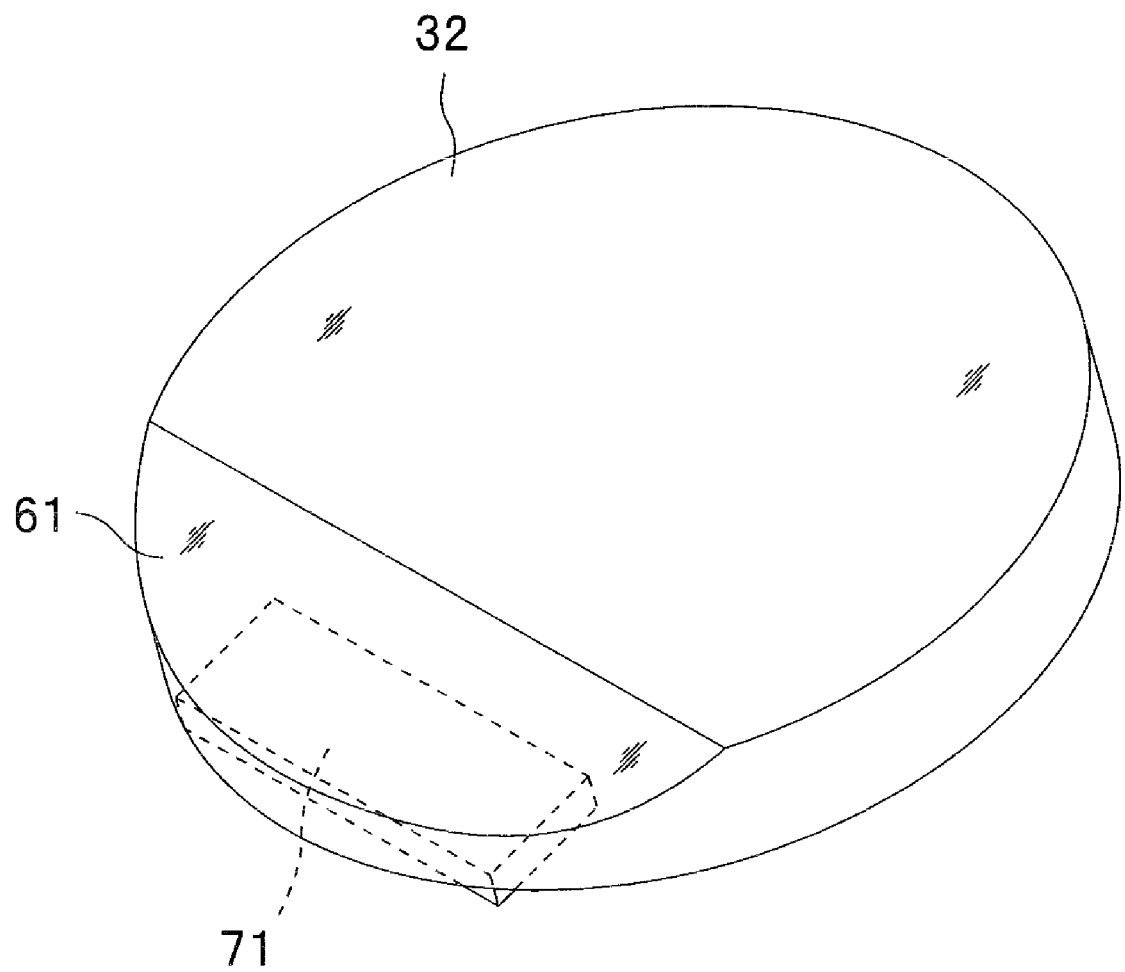
FIG. 13 is a perspective view showing an observation window and a piezoelectric ultrasonic transducer according to a second embodiment of the present invention.
Figure 14:
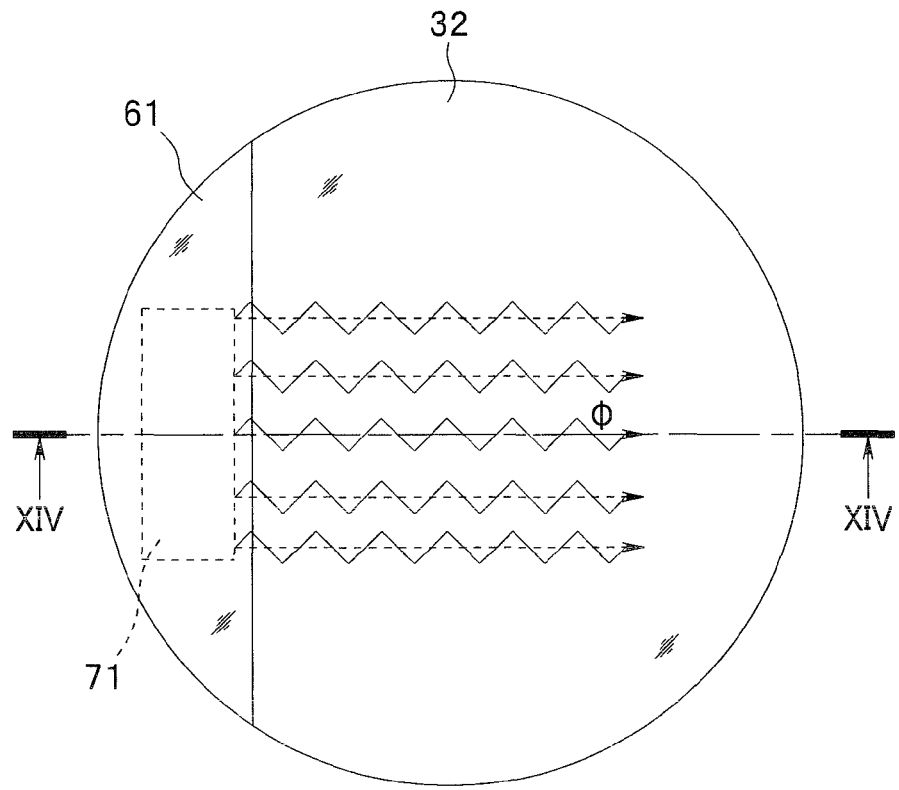
FIG. 14 is a plan view showing the observation window and the piezoelectric ultrasonic transducer in FIG. 13, according to the second embodiment.
Figure 15:
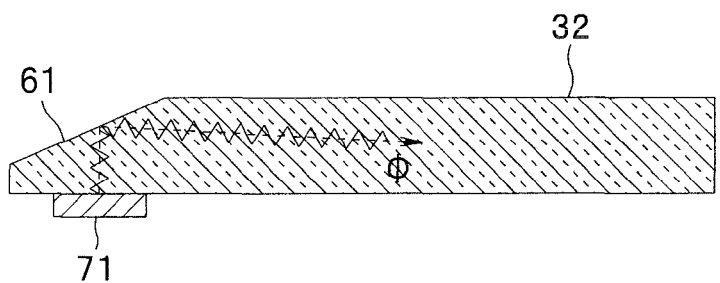
FIG. 15 is a cross-sectional view showing the observation window and the piezoelectric ultrasonic transducer taken along line XIV-XIV in FIG. 14, according to the second embodiment.
Figure 16:
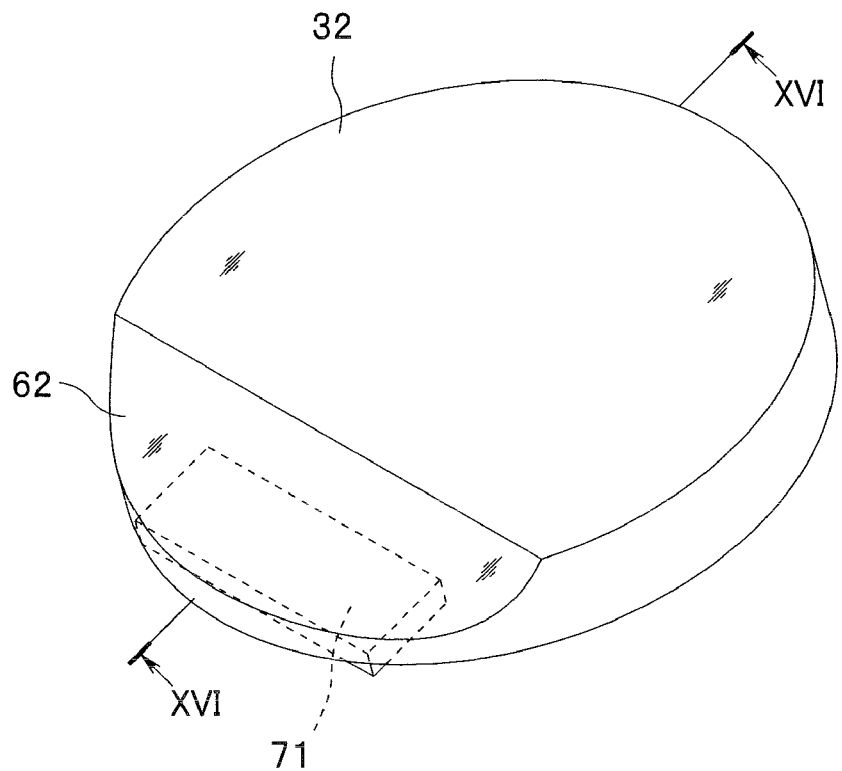
FIG. 16 is a perspective view showing the observation window and the piezoelectric ultrasonic transducer according to a first modification of the second embodiment.
Figure 17:
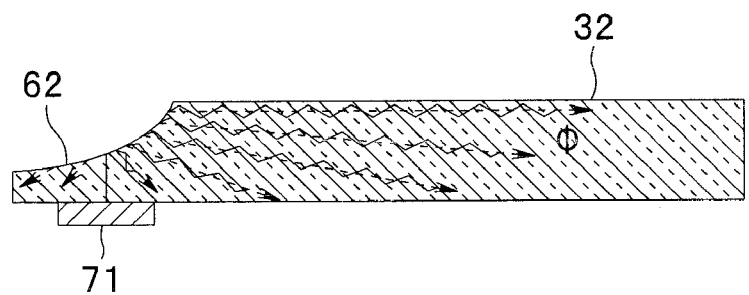
FIG. 17 is a cross-sectional view showing the observation window and the piezoelectric ultrasonic transducer taken along line XVI-XVI in FIG. 16, according to the first modification.
Figure 18:
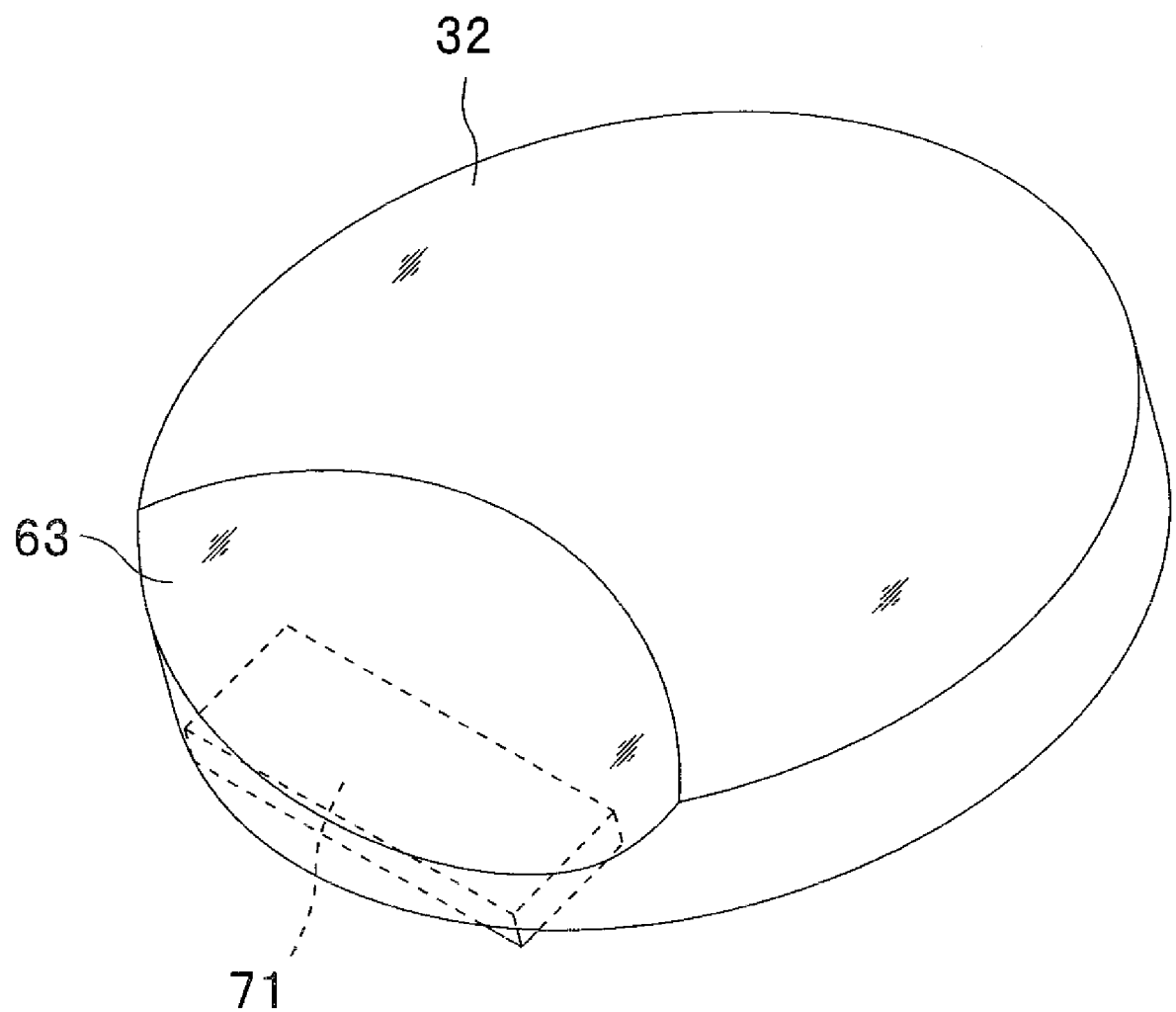
FIG. 18 is a perspective view showing the observation window and the piezoelectric ultrasonic transducer according to a second modification of the second embodiment.
Figure 19:
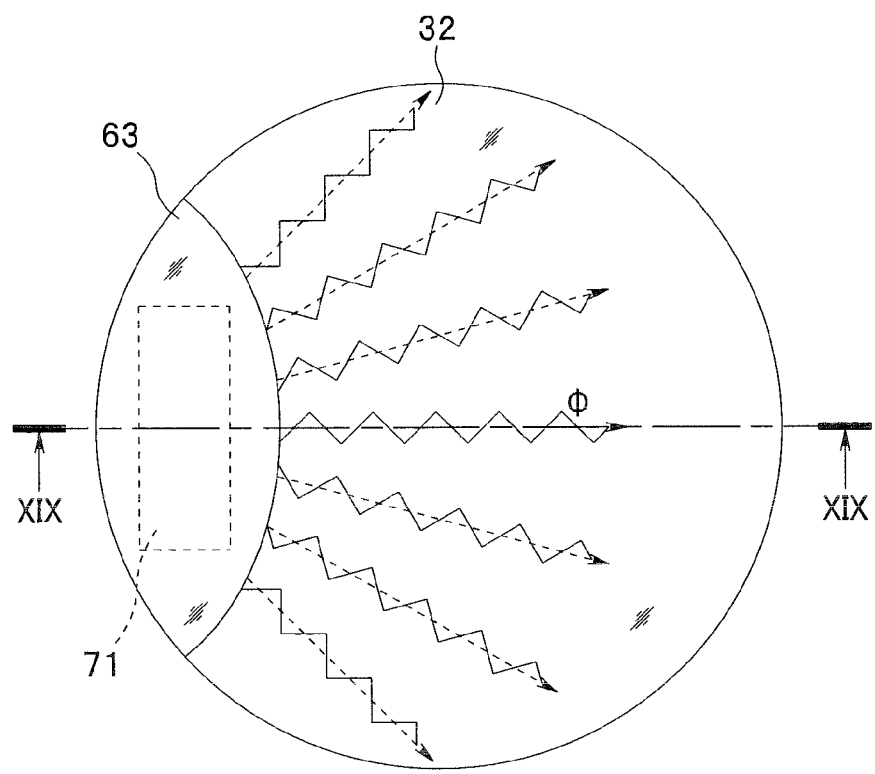
FIG. 19 is a plan view showing the observation window and the piezoelectric ultrasonic transducer in FIG. 18 according to the second modification.
Figure 20:
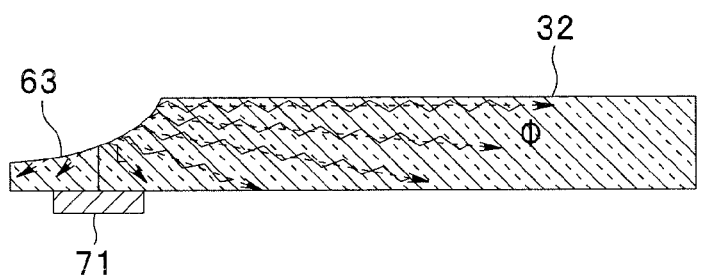
FIG. 20 is a cross-sectional view showing the observation window and the piezoelectric ultrasonic transducer taken along line XIX-XIX in FIG. 19, according to the second modification.
Figure 21:
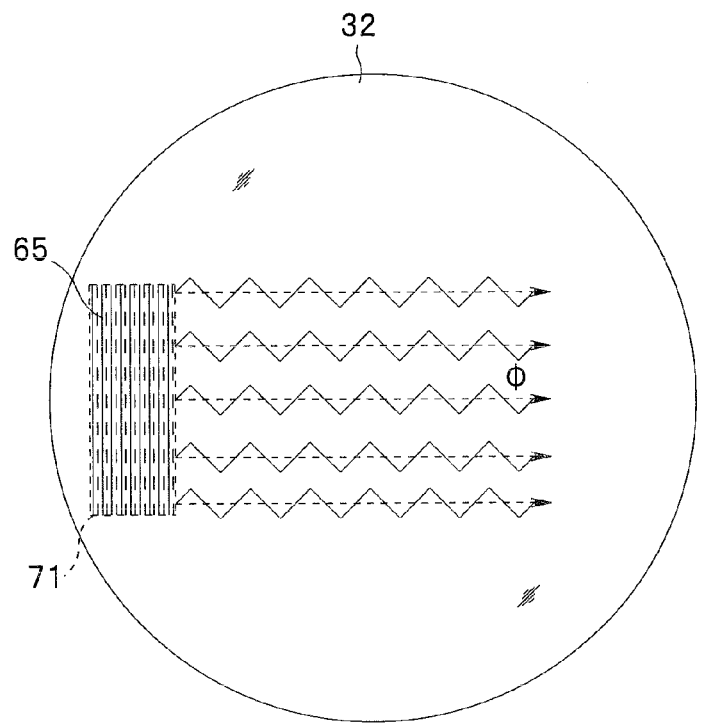
FIG. 21 is a plan view showing the observation window and the piezoelectric ultrasonic transducer according to a third modification of the second embodiment.
Figure 22:
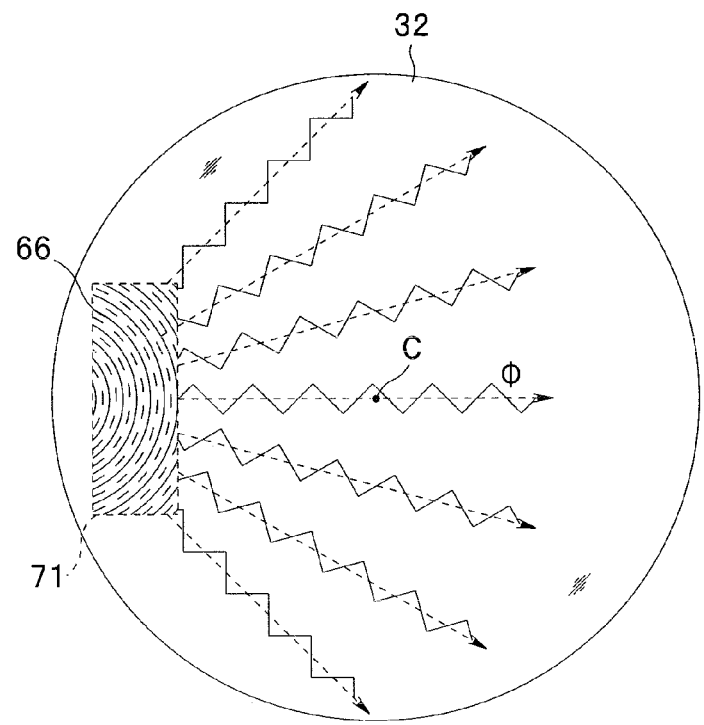
FIG. 22 is a plan view showing the observation window and the piezoelectric ultrasonic transducer according to a fourth modification of the second embodiment.

A second embodiment of an endoscope system 1 according to the present invention will be described in detail below with reference to FIGS. 13 to 22. FIGS. 13 to 22 relate to the second embodiment of the present invention. FIG. 13 is a perspective view showing an observation window and a piezoelectric ultrasonic transducer. FIG. 14 is a plan view showing the observation window and the piezoelectric ultrasonic transducer in FIG. 13. FIG. 15 is a cross-sectional view showing the observation window and the piezoelectric ultrasonic transducer taken along line XIV-XIV in FIG. 14. FIG. 16 is a perspective view showing the observation window and the piezoelectric ultrasonic transducer according to a first modification. FIG. 17 is a cross-sectional view showing the observation window and the piezoelectric ultrasonic transducer taken along line XVI-XVI in FIG. 16. FIG. 18 is a perspective view showing the observation window and the piezoelectric ultrasonic transducer according to a second modification. FIG. 19 is a plan view showing the observation window and the piezoelectric ultrasonic transducer in FIG. 18. FIG. 20 is a cross-sectional view showing the observation window and the piezoelectric ultrasonic transducer taken along line XIX-XIX in FIG. 19. FIG. 21 is a plan view showing the observation window and the piezoelectric ultrasonic transducer according to a third modification. FIG. 22 is a plan view showing the observation window and the piezoelectric ultrasonic transducer according to a fourth modification.

Note that, in a description of the present embodiment, components described in the first embodiment will be denoted by same reference numerals, and a description of a configuration and operation of the components will be omitted. A piezoelectric ultrasonic transducer provided in an endoscope 2 according to the present embodiment is not a ring-like one as in the first embodiment, and a piezoelectric ultrasonic transducer 71 whose wave emitting surface is rectangular is used.

As shown in FIGS. 13 to 15, a deflection portion which changes a direction of propagation of an ultrasonic wave ϕ from the piezoelectric ultrasonic transducer 71 provided on an inner surface of a glass plate 32 serving as an observation window is an inclined surface 61 formed by cutting away a part of an outer peripheral portion on an outer surface side of the glass plate 32. The inclined surface 61 is formed to slope down from an outer surface of the glass plate 32 toward an outer periphery.

A position of the inclined surface 61 relative to the rectangular piezoelectric ultrasonic transducer 71 is set to efficiently propagate the ultrasonic wave ϕ through the glass plate 32, like the first embodiment. More specifically, at least a part of a wave emitting surface of the piezoelectric ultrasonic transducer 71 needs to be within a projection region of the inclined surface 61 when the inclined surface 61 is projected from the surface (outer surface) where the inclined surface 61 is formed onto the surface (inner surface) of the glass plate 32 where the piezoelectric ultrasonic transducer 71 is attached. Preferably, the wave emitting surface of the piezoelectric ultrasonic transducer 71 is entirely within the projection region.

The endoscope system 1 according to the present embodiment with the above-described configuration is capable of easily removing a stain deposited on the outer surface of the glass plate 32 by efficiently deflecting the direction of propagation of the ultrasonic wave ϕ from the rectangular piezoelectric ultrasonic transducer 71 toward a part facing a region of an observation field of view of an image pickup module 34 (not shown here) in the glass plate 32 by the inclined surface 61 of the glass plate 32 provided in the endoscope 2, like the first embodiment. Since the piezoelectric ultrasonic transducer 71 is rectangular, processing of the inclined surface 61 to be formed at the glass plate 32 is advantageously easy, as compared to a case as in the first embodiment where the ring-like inclined surface 32a is provided at the glass plate 32.

Note that the deflection portion provided at the outer surface of the glass plate 32 serving as the observation window which changes the direction of propagation of the ultrasonic wave ϕ from the piezoelectric ultrasonic transducer 71 may be an inclined surface 62 whose cross-sectional surface is curved, as shown in FIGS. 16 and 17 as a first modification. Note that although a curved shape of the inclined surface 62 may be a shape curved away from or toward the inner surface of the glass plate 32, a concave curved surface as shown in FIG. 17 is preferable. In the case, the ultrasonic waves ϕ from the piezoelectric ultrasonic transducer 71 are reflected through a thickness of the glass plate 32, i.e., in various directions, and the ultrasonic waves ϕ are transmitted over a wider range. A curved shape like that of the inclined surface 62 may be applied to the ring-like inclined surface 32a constituting the deflection portion corresponding to the ring-like piezoelectric ultrasonic transducer 37 in the first embodiment.

The deflection portion provided at the outer surface of the glass plate 32 serving as the observation window which changes the direction of propagation of the ultrasonic wave φ from the piezoelectric ultrasonic transducer 71 may be an inclined surface 63 having a shape serving as a part of a surface of a spheroid, as shown in FIGS. 18 to 20 as a second modification. That is, the inclined surface 63 serving as the deflection portion has curvatures in two directions. In the case, the ultrasonic waves φ from the piezoelectric ultrasonic transducer 71 are deflected not only through the thickness of the glass plate 32 but also in directions spreading two-dimensionally as seen from above the glass plate 32, as shown in FIGS. 19 and 20. It is thus possible to propagate the ultrasonic waves φ over a wide range of the glass plate 32.

With the above-described configuration, the ultrasonic waves φ from the piezoelectric ultrasonic transducer 71 are propagated to the part facing the region of the observation field of view of the image pickup module 34 in the glass plate 32 by the inclined surface 63, which two-dimensionally diffuses the ultrasonic waves φ. Accordingly, even if the piezoelectric ultrasonic transducer 71 and inclined surface 63 are smaller than the piezoelectric ultrasonic transducer and inclined surface in each of the embodiments, it is possible to propagate the ultrasonic waves φ for removing a stain deposited on the outer surface of the glass plate 32 across a whole of the part facing the region of the observation field of view.

The deflection portion provided at the outer surface of the glass plate 32 serving as the observation window which changes the direction of propagation of the ultrasonic wave φ from the piezoelectric ultrasonic transducer 71 may be composed of grooves provided at the outer surface of the glass plate 32 as described with reference to FIGS. 10, 11, and 12 in the first embodiment, as shown in FIG. 21 as a third modification and FIG. 22 as a fourth modification. Grooves 65 (or 66) are configured such that at least a part of the wave emitting surface of the piezoelectric ultrasonic transducer 71 is located within a projection region of the grooves 65 (or 66) when the grooves 65 (or 66) are projected from the surface (outer surface) where the grooves 65 (or 66) are formed onto the surface (inner surface) of the glass plate 32 where the piezoelectric ultrasonic transducer 71 is attached.

The grooves 65 which are grooves in FIG. 21 are composed of linear grating-like asperities which deflect the direction of propagation of the ultrasonic wave 4 from the piezoelectric ultrasonic transducer 71 toward the part facing the region of the observation field of view of the image pickup module 34 in the glass plate 32. Cross-sectional shapes of the straight lines are rectangular or blazed, like the grooves shown in FIGS. 10 and 12. A period of the grooves is set such that a diffraction (deflection) direction of the ultrasonic wave φ is a specific direction. Especially when a surface acoustic wave is to be propagated at the outer surface of the glass plate, the period is about a value obtained by dividing velocity of a surface acoustic wave which propagates at the surface of the glass plate 32 by a frequency of the ultrasonic wave φ incident on the grating, like the grooves shown in FIG. 11.

The grooves 66 which are grooves in FIG. 22 are formed of curved lines having a curvature to be convex toward the center of the part facing the region of the observation field of view of the image pickup module 34, i.e., an intersection C of an optical axis of the image pickup module 34 and the outer surface of the glass plate 32, in order to deflect the directions of propagation of the ultrasonic waves φ from the piezoelectric ultrasonic transducer 71 toward the part facing the region of the observation field of view of the image pickup module 34 in the glass plate 32 for two-dimensional diffusion. Cross-sectional shapes of the grooves 66 are rectangular or blazed, like the grooves shown in FIGS. 10 and 12. A grating period is set such that the diffraction (deflection) direction of the ultrasonic wave φ is the specific direction. Especially when a surface acoustic wave is to be propagated at the outer surface of the glass plate, the grating period is about a value obtained by dividing velocity of a surface acoustic wave which propagates at the surface of the glass plate 32 by a frequency of the ultrasonic wave φ incident on the grating, like the grooves shown in FIG. 11.

As can be seen from the foregoing, the endoscope system 1 according to the present embodiment is capable of efficiently propagating the ultrasonic wave φ for stain removal from the rectangular piezoelectric ultrasonic transducer 71 toward the part facing the region of the observation field of view of the image pickup module 34 in the glass plate 32 serving as the observation window of the endoscope 2.

Note that, in each of the above-described embodiments, removal of the stain 101 is performed by a combination of the ultrasonic waves φ from the piezoelectric ultrasonic transducer 37 or 71 and supply of cleaning water W by the water supply sheath 3. At the time, the cleaning water W is supplied to the outer surface of the glass plate 32 in advance, and the piezoelectric ultrasonic transducer 37 or 71 is driven while the cleaning water W is supplied, thereby mixing the stain with the cleaning water. A part of the stain mixed with the cleaning water is atomized due to the waves from the piezoelectric ultrasonic transducer 37 or 71, and another part is washed away. In the manner, the stain 101 is separated and removed. After the removal of the stain 101, the supply of the cleaning water may be first stopped, the cleaning water W left on the outer surface of the glass plate 32 may be then vaporized by heat generated by the ultrasonic waves φ, and driving of the piezoelectric ultrasonic transducer 37 or 71 may be finally stopped. This makes it possible to achieve good visibility without water droplets left on the outer surface of the glass plate 32.

The inventions described in the context of the above-described embodiments are not limited to the embodiments and modifications, and various modifications can be made at an implementation stage without departing from scope of the present invention. The embodiments include inventions of various stages, and various inventions can be extracted by appropriately combining a plurality of disclosed constituent features.

For example, even if some constituent features are omitted from all the constituent features shown in the embodiments, a configuration from which the constituent features have been omitted can be extracted as an invention as long as the problem described above can be solved, and the effect described above can be achieved.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope apparatus comprising:
   a transparent member provided at a distal end of an insertion portion of an endoscope to face an image pickup optical system;
   an ultrasonic transducer attached to an inner surface of the transparent member; and a deflection portion provided at an outer surface of the transparent member which changes a direction of propagation of an ultrasonic wave from the ultrasonic transducer;

wherein the deflection portion changes a direction of propagation of at least some of ultrasonic waves generated from the ultrasonic transducer to a direction inside or at a surface of the transparent member toward a center of a part facing the image pickup optical system and the deflection portion comprises a reflecting surface which is formed at the outer surface of the transparent member and is composed of an inclined surface inclined at a predetermined angle with respect to the surface where the ultrasonic transducer is attached or a curved surface.

2. An endoscope apparatus comprising:

a transparent member provided at a distal end of an insertion portion of an endoscope to face an image pickup optical system;

an ultrasonic transducer attached to an inner surface of the transparent member; and a deflection portion provided at an outer surface of the transparent member which changes a direction of propagation of an ultrasonic wave from the ultrasonic transducer;

wherein the deflection portion changes a direction of propagation of at least some of ultrasonic waves generated from the ultrasonic transducer to a direction inside or at a surface of the transparent member toward a center of a part facing the image pickup optical system and the deflection portion comprises grating-like grooves formed at the outer surface of the transparent member.

3. The endoscope apparatus according to claim 2, wherein a period of the grating-like grooves is about a value obtained by dividing velocity of a surface acoustic wave which propagates at the outer surface of the transparent member by a frequency of the ultrasonic wave incident on the grating-like grooves when the ultrasonic wave is converted into the surface acoustic wave by the deflection portion.

4. The endoscope apparatus according to claim 2, wherein cross-sectional shapes of the grating-like grooves are blazed.

5. The endoscope apparatus according to claim 2, wherein the grating-like grooves comprises curved lines having a curvature to be convex toward an intersection of an optical axis of the image pickup optical system and the outer surface of the transparent member.

6. The endoscope apparatus according to claim 3, wherein the grating-like grooves comprises curved lines having a curvature to be convex toward an intersection of an optical axis of the image pickup optical system and the outer surface of the transparent member.

7. The endoscope apparatus according to claim 4, wherein the grating-like grooves comprises curved lines having a curvature to be convex toward an intersection of an optical axis of the image pickup optical system and the outer surface of the transparent member.

8. An endoscope apparatus comprising:

a transparent member provided at a distal end of an insertion portion of an endoscope to face an image pickup optical system;

an ultrasonic transducer attached to an inner surface of the transparent member; and a deflection portion provided at an outer surface of the transparent member which changes a direction of propagation of an ultrasonic wave from the ultrasonic transducer;

wherein the deflection portion changes a direction of propagation of at least some of ultrasonic waves generated from the ultrasonic transducer to a direction inside or at a surface of the transparent member across a whole of an observation region of the image pickup optical system in the transparent member and the deflection portion comprises a reflecting surface which is formed at the outer surface of the transparent member and is composed of an inclined surface inclined at a predetermined angle with respect to the surface where the ultrasonic transducer is attached or a curved surface.

9. An endoscope apparatus comprising:

a transparent member provided at a distal end of an insertion portion of an endoscope to face an image pickup optical system;

an ultrasonic transducer attached to an inner surface of the transparent member; and a deflection portion provided at an outer surface of the transparent member which changes a direction of propagation of an ultrasonic wave from the ultrasonic transducer;

wherein the deflection portion changes a direction of propagation of at least some of ultrasonic waves generated from the ultrasonic transducer to a direction inside or at a surface of the transparent member across a whole of an observation region of the image pickup optical system in the transparent member, the deflection portion comprises grating-like grooves formed at the outer surface of the transparent member and a period of the grating-like grooves is about a value obtained by dividing velocity of a surface acoustic wave which propagates at the outer surface of the transparent member by a frequency of the ultrasonic wave incident on the grating-like grooves when the ultrasonic wave is converted into the surface acoustic wave by the deflection portion.

10. An endoscope apparatus comprising:

a transparent member provided at a distal end of an insertion portion of an endoscope to face an image pickup optical system;

an ultrasonic transducer attached to an inner surface of the transparent member; and a deflection portion provided at an outer surface of the transparent member which changes a direction of propagation of an ultrasonic wave from the ultrasonic transducer;

wherein the deflection portion changes a direction of propagation of at least some of ultrasonic waves generated from the ultrasonic transducer to a direction inside or at a surface of the transparent member across a whole of an observation region of the image pickup optical system in the transparent member, the deflection portion comprises grating-like grooves formed at the outer surface of the transparent member and cross-sectional shapes of the grating-like grooves are blazed.

11. An endoscope apparatus comprising:

a transparent member provided at a distal end of an insertion portion of an endoscope to face an image pickup optical system;

an ultrasonic transducer attached to an inner surface of the transparent member; and a deflection portion provided at an outer surface of the transparent member which changes a direction of propagation of an ultrasonic wave from the ultrasonic transducer;

wherein the deflection portion changes a direction of propagation of at least some of ultrasonic waves generated from the ultrasonic transducer to a direction inside or at a surface of the transparent member across a whole of an observation region of the image pickup optical system in the transparent member, the deflection portion comprises grating-like grooves formed at the outer surface of the transparent member and the grating-like grooves comprises curved lines having a curvature to be convex toward an intersection of an optical axis of the image pickup optical system and the outer surface of the transparent member.

12. The endoscope apparatus according to claim 9, wherein the grating-like grooves comprises curved lines having a curvature to be convex toward an intersection of an optical axis of the image pickup optical system and the outer surface of the transparent member.

13. The endoscope apparatus according to claim 10, wherein the grating-like grooves comprises curved lines having a curvature to be convex toward an intersection of an optical axis of the image pickup optical system and the outer surface of the transparent member.

* * * * *